(12) United States Patent
Franchi et al.

(10) Patent No.: US 8,513,310 B2
(45) Date of Patent: *Aug. 20, 2013

(54) COSMETIC USE OF PHYTOSPHINGOSINE AS SLIMMING AGENT AND COSMETIC COMPOSITIONS COMPRISING PHYTOSPHINGOSINE

(75) Inventors: Jocelyne Franchi, Orleans (FR); Françoise Pellicier, Loury (FR)

(73) Assignee: LVMH Recherche, Saint Jean de Braye (FR)

( * ) Notice: Subject to any disclaimer, the term of this patent is extended or adjusted under 35 U.S.C. 154(b) by 506 days.

This patent is subject to a terminal disclaimer.

(21) Appl. No.: 12/773,365

(22) Filed: May 4, 2010

(65) Prior Publication Data
US 2010/0233298 A1    Sep. 16, 2010

Related U.S. Application Data

(63) Continuation of application No. 10/506,407, filed as application No. PCT/FR03/00656 on Feb. 28, 2003, now Pat. No. 7,737,186.

(30) Foreign Application Priority Data

Mar. 1, 2002  (FR) ..................................... 02 02675

(51) Int. Cl.
| | |
|---|---|
| *A01N 31/00* | (2006.01) |
| *A01N 33/18* | (2006.01) |
| *A01N 33/24* | (2006.01) |
| *A01N 65/00* | (2009.01) |
| *A61K 31/045* | (2006.01) |
| *A61K 8/02* | (2006.01) |
| *A61K 36/00* | (2006.01) |

(52) U.S. Cl.
USPC ............ 514/738; 514/727; 424/401; 424/725

(58) Field of Classification Search
USPC .......................... 514/738, 727; 424/401, 725
See application file for complete search history.

(56) References Cited

U.S. PATENT DOCUMENTS 5,578,641 A * 11/1996 Jackson et al. ................ 514/547
5,679,358 A * 10/1997 Bombardelli et al. ........ 424/401

* cited by examiner

*Primary Examiner* — Kendra D Carter
(74) *Attorney, Agent, or Firm* — Nath, Goldberg & Meyer; Tanya E. Harkins

(57) ABSTRACT

The invention relates to novel cosmetic uses of phytosphingosine or of one of its cosmetically acceptable salts, particularly its hydrochloride, as a slimming agent and/or as an active agent which stimulates the synthesis of leptin by adipocytes, for preparing a cosmetic composition intended for reducing subcutaneous excess fat.

Figure 1:
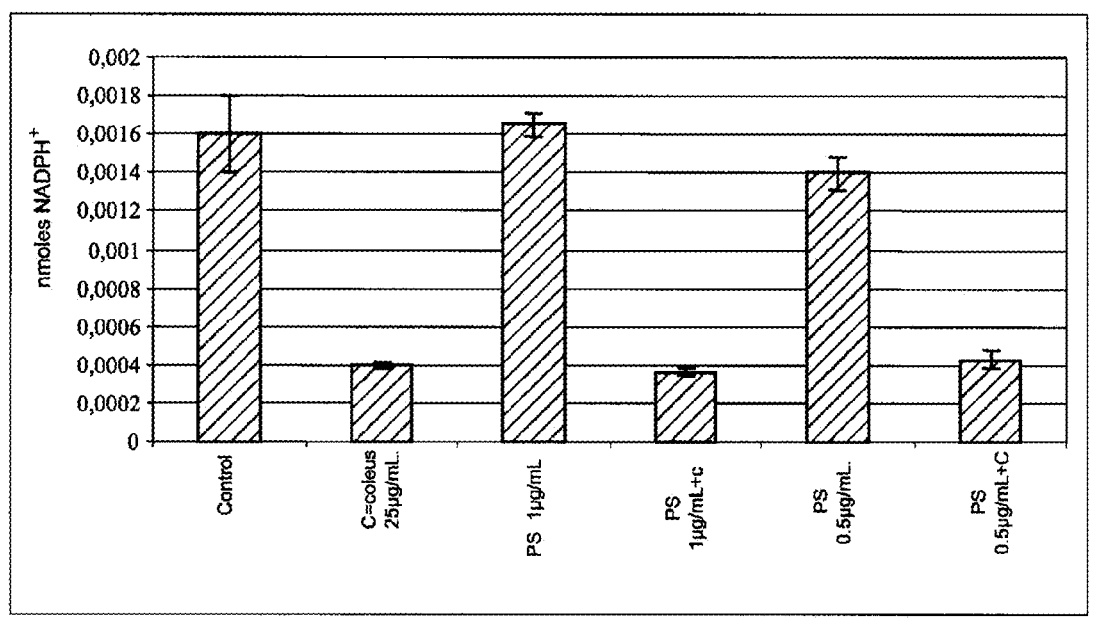

The invention also relates to a method of cosmetic treatment intended for obtaining a slimming effect on the human body according to which a cosmetic composition containing phytosphingosine or one of its cosmetically acceptable salts, particularly its hydrochloride, is applied on the parts of the body to be treated.

The invention also relates to novel cosmetic compositions containing phytosphingosine or one of its cosmetically acceptable salts, particularly its hydrochloride, in combination with a lipolytic agent selected from the group consisting of CAMP and its derivatives, adenylate cyclase enzyme activating agents and phosphodiesterase enzyme inhibiting agents.

17 Claims, 6 Drawing Sheets

COSMETIC USE OF PHYTOSPHINGOSINE AS SLIMMING AGENT AND COSMETIC COMPOSITIONS COMPRISING PHYTOSPHINGOSINE

This is a Continuation Application of U.S. patent application Ser. No. 10/506,407, filed Sep. 1, 2004, which was filed under 35 U.S.C. 371 as a national stage of PCT/FR03/00656, filed Feb. 28, 2003, the content of each of which is hereby incorporated by reference in its entirety.

The present invention relates to a novel cosmetic use of phytosphingosine, as a slimming agent, as well as to cosmetic compositions containing phytosphingosine.

Phytosphingosine is of the following formula:

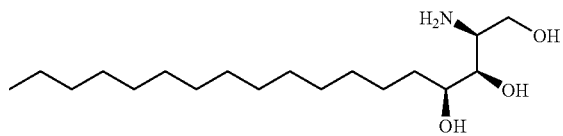 [SMILES: CCCCCCCCCCCCCC[C@H](O)[C@H](O)[C@@H](N)CO]

Its molecular formula is $C_{18}H_{39}NO_3$ and its CAS number is as follows: RN 100 000 403-19-8

This product is also known under the designation: (2S,3S,4R)-2-amino-1,3,4-octadecanetriol.

Phytosphingosine is a commercial product which corresponds to one of the three sphingoid bases which are present naturally in the skin, phytosphingosine being present in the stratum corneum.

Applications of phytosphingosine and of its salts, and, more particularly, of its hydrochloride, are already known in the field of dermatology. Phytosphingosine is in fact known essentially for its anti-microbial activity, as well as for its activity as a <<second messenger>>, which is an application which results in a reduction of the sensitivity of the skin. More specifically, phytosphingosine is known for its activity in the treatment of acne, for its activity of inhibiting the growth of microorganisms on the skin, and for reducing various inflammatory phenomena observed on the skin.

The inventors of the present invention have, in an entirely surprising way, now discovered a novel use of phytosphingosine, as well as of its cosmetically acceptable salts, particularly of its hydrochloride, as a slimming agent. They have furthermore demonstrated that this novel use is linked, at least partially, to the perfectly unexpected property of phytosphingosine, and of its salts, of promoting the synthesis of leptin by adipocytes of the skin.

Furthermore, in pursuing their studies in this field, the inventors of the present invention have also demonstrated that a certain number of combinations of phytosphingosine or of its cosmetically acceptable salts turned out to be particularly interesting in these novel uses.

Leptin from the mouse has recently been identified in 1994 as being the product of the "ob gene" (Zhang, y et al., Nature, 1994, 372:425 and Tartaglia L. A., 1997, J. Biol. Chem. 272:6093).

The structure of human leptin (or human OB protein) and its use in the modulation of weight in animals are described in British patent application GB 2,292,382. Leptin is a protein which is secreted by the adipocyte which informs the brain of the state of the adipose reserves. It acts through membrane receptors which are situated in particular in the hypothalamus.

Leptin was first studied in the rodent and then in man, and plays a key role in the regulation of body weight.

In ob/ob mice, the absence of leptin in the serum, due to mutations of the ob gene (that which encodes leptin), leads to a massive obesity.

In man, the first pieces of work in relation to leptin were directed towards obese and/or diabetic patients.

In fact, the more an adipocyte possesses a higher content of triglycerides, the more it produces leptin, and vice versa (Medecine/Sciences, 1998, n° 8-9, 14, 858-864, G. Ailhaud: L'adipocyte, cellule secrétrice and endocrine (<<The adipocyte, a secretory and endocrine cell>>)).

Thus, in the obese person, two situations can arise. Either a mutation of the leptin gene exists, this mutation is then non-functional, particularly on the receptors in the brain, or, a lack of transfer of leptin exists about the blood-brain barrier.

One study, during which a daily injection of synthetic leptin was made in patients suffering from obesity or from excess weight, has shown conclusive results: a significant weight loss appeared in patients suffering from a certain form of obesity (work carried out at Tufts University in the USA, presented on the occasion of the conference: American Diabetes Association: Jean Mayer, USA Human Nutrition Research Center on Aging).

Leptin does in fact trigger off a phenomenon of satiety which causes a reduction in food ingestion and which reduces the frequency of food ingestion.

When the adipose mass increases, the leptin produced by the adipose tissue will inhibit the food ingestion and will stimulate energy expenditure. Leptin will thus act against an excessive weight gain.

Hence, it may be considered that this protein is a regulator of the adipose mass, the prime role of which is to inhibit the deposit of excess adiposity.

The role of local regulation which is played by leptin is well-known (see Systemically and Topically Administered Leptin Both Accelerate Wound Healing in Diabetic ob/ob Mice. B. D. Ring, S. Scully, C. R. Davis, M. B Baker, M. J. Cullen, M. A. Pelleymounter, D. Danilenko. Endocrinology, 2000 vol. 141, n° 1, p. 446-449).

Furthermore, the role of leptin in the expression of certain genes leading to the accumulation of lipids (differentiation genes) is also well-known within the context of regulation of lipolysis.

Leptin on the one hand suppresses the expression of certain genes leading to an accumulation of lipids (differentiation genes), and this takes place without the participation of the brain.

On the other hand, leptin induces a lipolysis directly on the adipocytes. This has been observed on mouse adipocytes in vitro (see In vitro Lipolytic Effect of Leptin on Mouse Adipocytes: Evidence for a possible Autocrine/Paracrine Role of Leptin, G. Frühbeck, M. Aguado, J. A. Martinez, Biochemical and Biophysical Research communications 1997: 240, p. 590-594). The effect of leptin on the lipolysis of the adipocytes is specific and operates via receptors which are present in the white adipose tissue.

Leptin converts oestrone of the blood circulation (a hormone which increases lipid deposits) into oleyl-oestrone which is considered to be a "slimming" factor. The appearance of this factor causes a generalised lipolysis and a thermogenesis (see Leptin enhances the synthesis of oleyl-estrone from estrone in white adipose tissue, M. Esteve, J. Virgili, H. Aguilar, F. Balada, J. A. Fernandez-Lopez, W. Remesar, M. Alemany, Eur J. Nutr. 1999, 38, p. 99-104). When oleyl-oestrone is administered to obese or normal rats, it causes a loss in fatty mass.

All the interest that there is thus seen in having a means available to act upon the synthesis of leptin, which will notably act:

directly on the skin via receptors present therein,
on the adipose tissue in causing lipolysis,
on a factor acting as a weight regulator, namely, oleyl-oestrone.

Tests carried out within the context of the present invention, on cultures of murine adipocytes as well as on cultures of human adipocytes, have enabled demonstrating that it was possible, by treating these cultures with phytosphingosine or one of its salts, particularly its hydrochloride, to stimulate the synthesis of leptin by these adipocytes, and this left predicting the possibility of using phytosphingosine or its salts as a slimming agent. It has been possible to confirm this effect.

Hence, according to a first aspect, the present invention relates to a novel cosmetic use of phytosphingosine or of one of its cosmetically acceptable salts, particularly its hydrochloride, as a slimming agent for preparing a cosmetic composition intended for reducing subcutaneous excess fat.

According to a second aspect, the invention relates to a novel cosmetic use of phytosphingosine or of one of its cosmetically acceptable salts, particularly of its hydrochloride, as an active agent which stimulates the synthesis of leptin by adipocytes, for preparing a cosmetic composition intended for reducing subcutaneous excess fat.

According to a third aspect, the invention relates to a method of cosmetic treatment intended for obtaining a slimming effect on the human body, according to which an effective amount of a cosmetic composition containing phytosphingosine or one of its cosmetically acceptable salts, particularly its hydrochloride, is applied on the parts of the body where said effect is sought.

Furthermore, according to the three aspects of the invention, as defined supra, it has appeared that certain combinations of phytosphingosine or of one of its cosmetically acceptable salts, particularly of its hydrochloride, turned out to be particularly interesting for improving the slimming effect obtained by the application of any one of the compositions containing these particular combinations.

More specifically, it has appeared that the combination of phytosphingosine or of one of its cosmetically acceptable salts, with one or more agents, hereinafter designated as lipolytic agents, which induce a lipolysis, in the adipocytes, turned out to be particularly interesting within the context of the present invention, as will be explained further on.

In particular, at least one cosmetically acceptable lipolytic agent will be selected from the group consisting of adenosine 3',5'-cyclic monophosphate (cAMP) and its derivatives, adenylate cyclase enzyme activating agents and phosphodiesterase enzyme inhibiting agents, for making this combination.

Forskolin, or a plant extract containing it, such as an extract of *Coleus forskohlii* or *Plectranthus barbatus*, or even an extract of the plant *Tephrosia purpurea*, will advantageously be selected as adenylate cyclase activating agent.

It will be possible to use a xanthine, such as 3-isobutyl-1-methyl-xanthine or IBMX, caffeine or theophilline, as phosphodiesterase inhibiting agent.

The cosmetic compositions containing such combinations, which are novel per se, constitute the fourth aspect of the invention. It is these compositions as they are defined infra which will preferably be made use of in all the cosmetic applications covered by the present invention.

Hence, according to this fourth aspect, the present invention relates to a cosmetic composition, notably intended for reducing subcutaneous excess fat, characterised in that it contains, as active agent, phytosphingosine, or one of its cosmetically acceptable salts, particularly its hydrochloride, and
at least one cosmetically acceptable lipolytic agent selected from the group consisting of cAMP and its cosmetically acceptable derivatives, adenylate cyclase enzyme activating agents and phosphodiesterase enzyme inhibiting agents, in a cosmetically acceptable vehicle.

In the novel compositions of the invention, which are also the compositions which are preferred for the implementation of the various applications covered by the present invention, phytosphingosine, or one of its cosmetically acceptable salts, particularly its hydrochloride, is contained in the cosmetic composition at a concentration of between 0.001% and 1% and, preferably, between 0.05% and 0.5% by weight with respect to the total weight of said composition.

The cosmetic composition further contains at least one lipolytic active agent selected from the group consisting of cAMP and its lipolytic derivatives, adenylate cyclase enzyme activating agents and phosphodiesterase enzyme inhibiting agents.

In these cosmetic compositions, cAMP or its derivative will advantageously be used at a concentration of between 0.001% and 5% by weight with respect to the total weight of the composition.

It will be possible to select any cosmetically acceptable derivative of cAMP, and particularly a salt or an acylated derivative, notably a mono- or dibutyryl derivative, as a derivative of cAMP.

Forskolin, or a plant extract containing it, preferably at a concentration of between 0.001% and 1% and, preferably between 0.05% and 0.25%, by weight with respect to the total weight of the composition, is advantageously selected as an adenylate cyclase enzyme activating agent.

An extract of *Coleus forskohlii* or *Plectranthus barbatus* will be preferably selected as an extract containing forskolin. Such an extract can be obtained by an extraction method, such as the one described in the International application WO 91/02516.

It will also be possible to use an extract of the plant *Tephrosia purpurea*, at a concentration of between 0.001% and 5%, preferably between 0.01% and 5%, by weight with respect to the total weight of the composition, as an adenylate cyclase activating agent. Such an extract can be obtained by an extraction method such as the one described in the International application WO 95/03780.

Finally, as set forth supra, according to another variant, the preferred compositions according to the invention contain a phosphodiesterase inhibiting agent, particularly a xanthine, and, more particularly, 3-isobutyl-1-methyl-xanthine (IBMX), caffeine or theophilline, preferably at a concentration of between 0.001% and 10%, preferably between 0.01 and 1%, by weight with respect to the weight of the composition.

The preferred compositions which are used in accordance with the present invention and which contain a combination of phytosphingosine or of one of its salts with a lipolytic agent such as cAMP and its lipolytic derivatives, adenylate cyclase activating agents and phosphodiesterase inhibiting agents, turn out to be particularly interesting by virtue of the synergistic action of the two types of constituents.

Without the inventors considering to be totally bound by this explanation, a plausible interpretation of the synergy effect observed is given infra.

It has in fact already been observed that the agents which promote a lipolysis in the adipocytes, such as the extracts of *Coleus* for example, possess a remarkable biological effectiveness which in general combines a significant lipolytic power with an inhibitory activity of adipocyte maturation. The significant reduction in volume and in quantity of the lipid vacuoles after a treatment with the lipolytic agent leads to a reduction in the production of leptin. It is thus probable that this local loss of leptin in the environment close to the adipocytes resulting from the treatment by the lipolytic agent might be compensated by the effect of a product which stimulates leptin synthesis, in the present case by phytosphingosine or its salt. The maintenance of a sufficient leptin concentration in the environment close to the adipocytes thus exerts a role with acts against the increase in the adipose mass. It thus seems that all takes place as though the message were emitted by fatty cells which inform, by a retro-control operation, of the necessity to reduce the storage in the form of triglycerides. Thus, by virtue of the combined action of phytosphingosine or of one of its salts, and of at least one other lipolytic agent, an increased and a longer-acting slimming effect is obtained.

This hypothesis does seem to be confirmed entirely by the results obtained within the context of Examples 2 and 4 of the present invention which concern the combination of phytosphingosine with an extract of *Coleus forskohlii*.

Figure 2:
Figure 3:
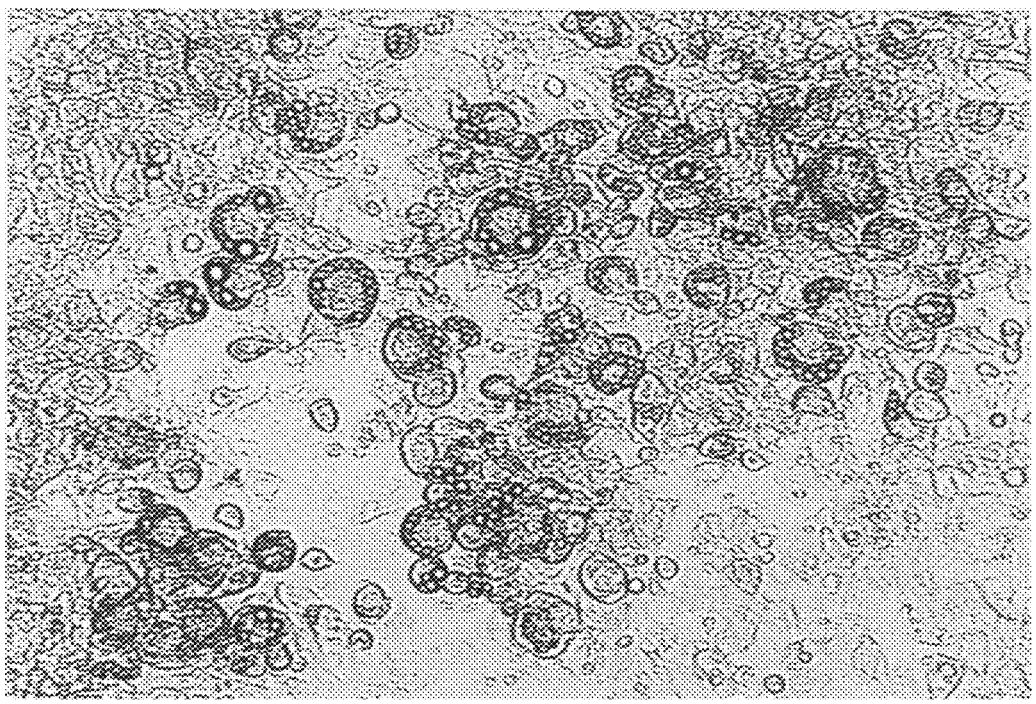
Figure 4:
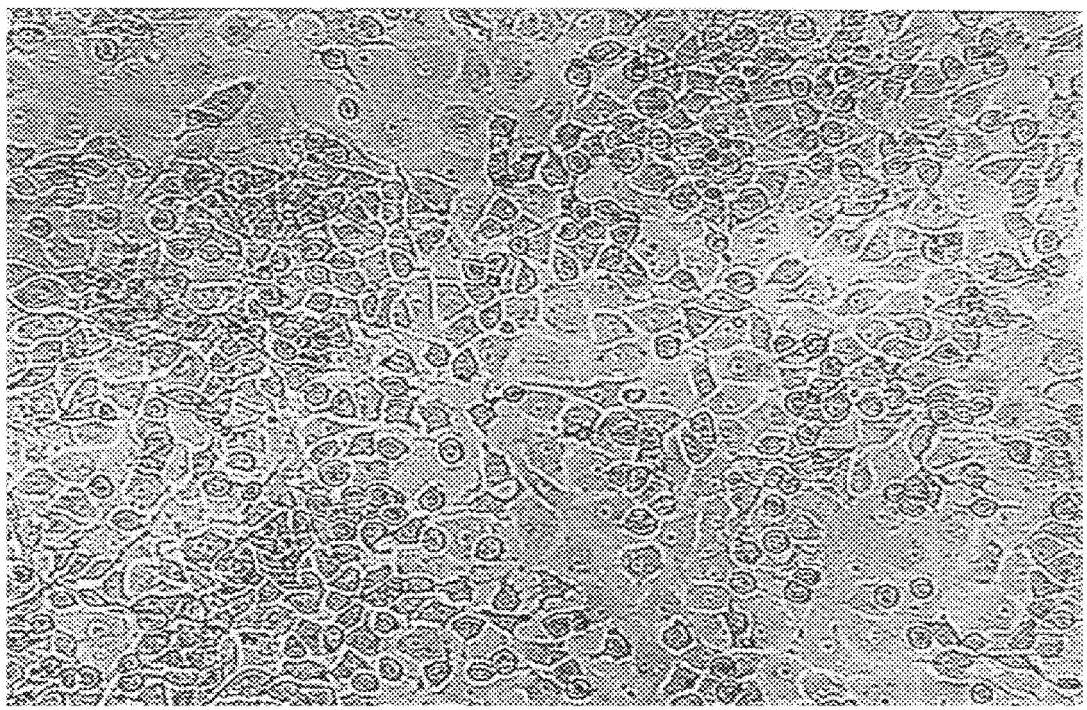
Figure 5:
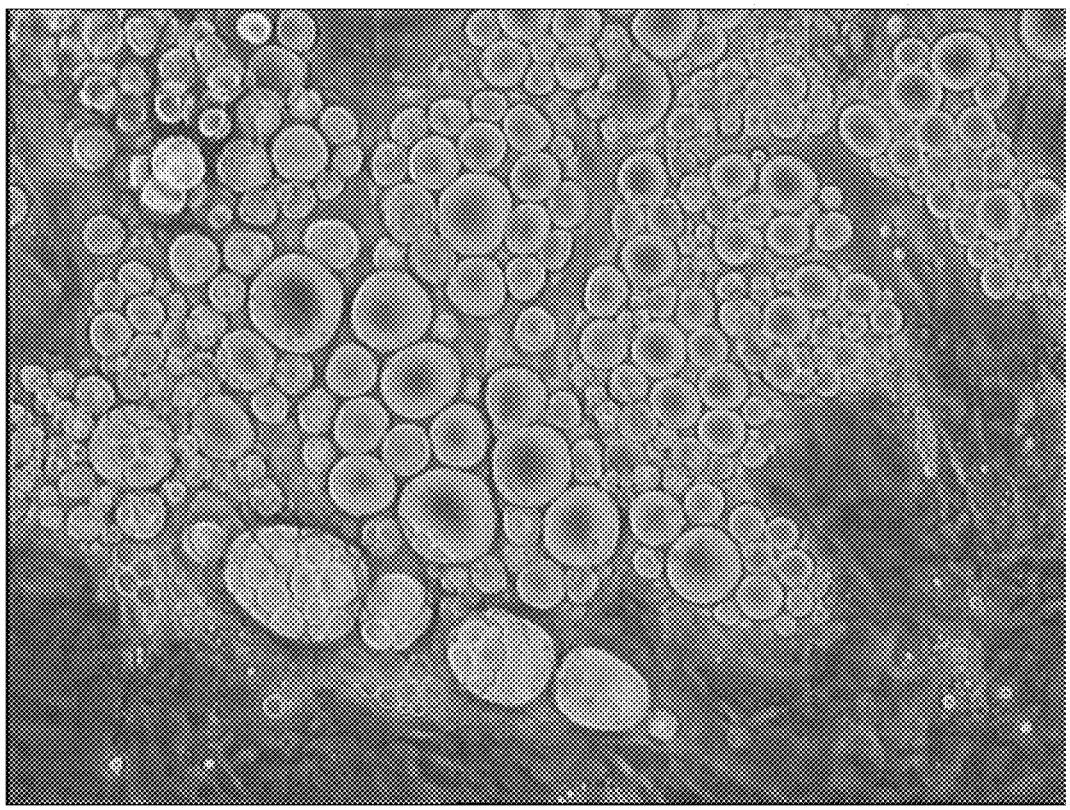
Figure 6:
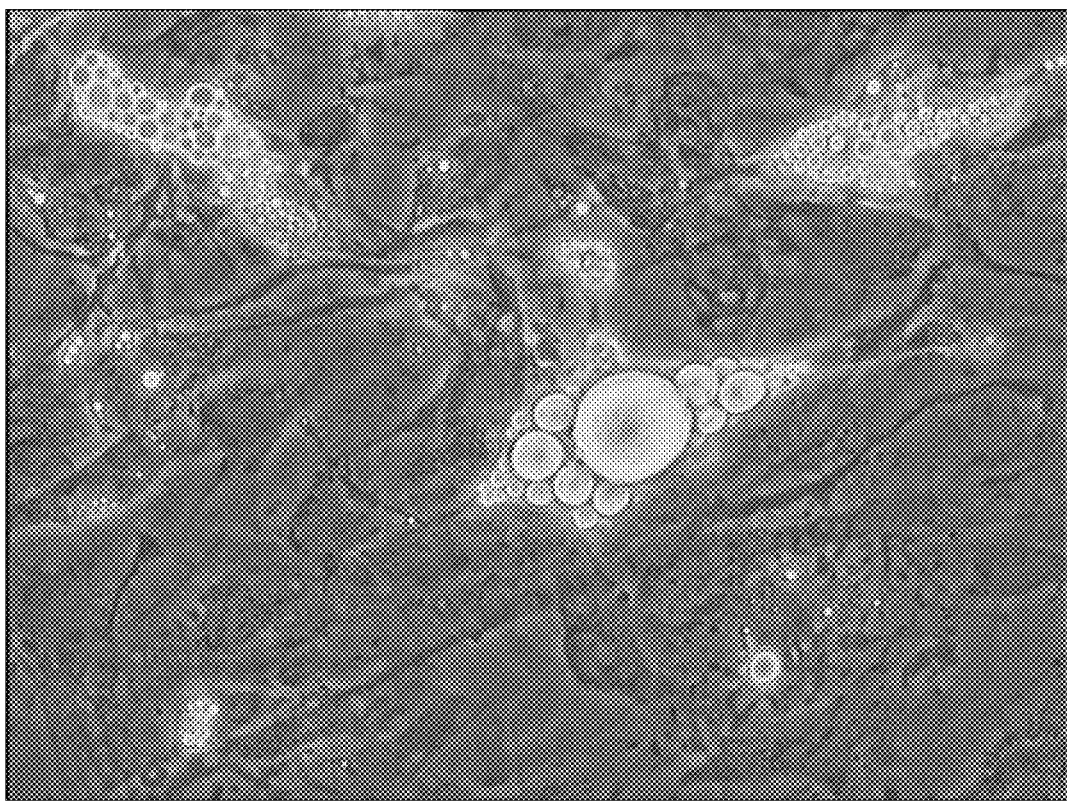

The following Examples are given purely as an illustration of the present invention. They are accompanied by FIGS. 1 to 6, which represent, respectively:

FIG. 1: the effect upon the lipogenesis of various treatments carried out in Example 2;

FIGS. 2 to 4: the morphology of the murine adipocytes at different stages of the treatment according to Example 2;

FIG. 5: the morphology of the human adipocytes at D18 for a control solution (according to Example 3); and FIG. 6: the morphology of the human adipocytes at D18 for a treatment with a combination according to the invention (according to Example 3).

EXAMPLES

In the following Examples, and, unless indicated otherwise, the proportions are indicated in percentage by weight.

Example 1

Demonstration of the stimulating activity of phytosphingosine on the production of leptin by murine adipocytes in culture.

1. Principle of the Test

The concept according to which the adipose mass may be regulated via secreted circulating factors is very interesting.

The principle of the test is to control the secretion of leptin by the adipocytes.

2. Material and Methods

Culture of 3T3 F442A Cells

A clone, which has the capacity to accumulate larger amounts of triglycerides, was isolated from an established cell-line of mouse 3T3 preadipocytes. The lipolytic agents reduce this accumulation. It thus appeared important to test potential lipolytic agents on this 3T3 F442A murine preadipocytes cell-line. These preadipocytes (GREEN H. and KEHINDE O.—Spontaneous Heritable Changes Leading to Increased Adipose Conversion in 3T3 Cells, Cell Vol. 7, 105-113, 1976) can multiply and differentiate by possessing the morphological and biochemical phenotype which is characteristic of the differentiated function of the mature adipocyte. When they are in exponential growth phase, they are of fibroblastic appearance, having an elongated shape and are very adherent to the support. At the confluence, when the conditions so permit, a very premature morphological transition gives them a rounded shape.

The cells thus undergo a clonal amplification process. Increases in the activity of lipogenetic enzymes are added to these morphological changes, as well as increases in responses by the cells to hormones/factors which affect the lipogenesis and the lipolysis.

The 3T3 F442A preadipocytes thus constitute an excellent model for study of lipolysis, by virtue of the morphological and metabolic transformations acquired by the cells during their development programme. (Pairault J and Lasnier F: Control of adipogenetic differenciation of 3T3 F442A cells by retinoic acid, dexamethasone and insulin: a topographic analysis J. cell Physiol. 1987, 132, 279-86).

According to the literature, leptin is secreted in the culture medium since it is stored in the adipocytes. (Wabitsch M et al, Diabetes, 1996, vol 45, Bornstein S. et al, Diabetes, 2000, vol 49, Friedman J M, Nutrition Reviews, 1998, vol 56 n° 2).

In 3T3 F442A cells, the expression of the ob gene has been studied in particular (Leroy P et al, J. of Biol. Chem., 1996, vol 271 n° 5, pp. 2365-2368, Considine R V et al,—Horm. Res. 1996, 46: 249-256).

The 3T3 F442A preadipocytes are shown at D0 in 35 mm Petri dishes (Corning) and placed in an oven at 37° C. under an air-$CO_2$ atmosphere (95-5). The cells are cultivated in an Eagle minimum essential medium modified according to Dulbecco (glucose 4.50 g/l) (DMEM-GIBCO BRL) supplemented with 5% of calf serum (CS) (BIOMEDIA®) and 5% of foetal calf serum (GIBCO) during the growth phase. The medium is changed at D2 and D4.

At the cell confluence (at D7), the medium is changed:

The basic medium remains the same (DMEM) but is supplemented with 10% of foetal calf serum (FCS) and insulin (5 µg/mL) (SIGMA).

The medium is then changed at D9 and D11.

At D14, D16 and D18, a treatment is made with the composition the effectiveness of which on the leptin synthesis it is sought to verify.

The protocol is summarised in the Table below:

| | |
|---|---|
| D0 | Sowing of the 3T3 F442A in DMEM, 5% CS, 5% FCS - cell density $2 \times 10^4$ cells/35 mm Petri dish |
| D2 | Change of medium |
| D4 | Change of medium |
| D7 | Confluence - Culture medium DMEM, 10% FCS, 1% insulin (mother solution at 500 µg/mL) |
| D9 and D11 | Change of medium |
| D14 | Treatment with the composition to be tested |
| D16 and D18 | Treatment with the composition to be tested |
| D21 | Collection of the cell supernatants |

3. Leptin Determination

The leptin secreted is determined by means of a sandwich-type Elisa technique re-running with a Quantikine M Mouse Leptin Immunoassay kit.

This ELISA determination uses recombined mouse leptin, expressed in *E. coli* and antibodies directed against recombinant mouse leptin.

The test uses a "sandwich" immunoenzymatic technique. The microplate wells are lined with a mouse leptin polyclonal antibody.

The standards, controls and samples are deposited in the wells and, at the same moment, all the leptin present binds to the immobilised antibody.

The bound leptin is then detected by a mouse anti-leptin antibody which is coupled to an enzyme peroxidase. A substrate solution is then added into the wells. The enzymatic reaction leads to a blue solution which turns yellow after addition of a quenching solution.

The intensity of the colour measured is proportional to the amount of leptin present. The reading of the optical density is done at 450 nm on the spectrophotometer.

The determination is obtained afterwards of the dose-response curves in relation to the measurement of natural leptin, parallel to the standard curves obtained with "recombinant" Quantikine M standards. The Quantikine M kit thus enables the relative mass values for the natural mouse leptin to be determined.

The optical density measured at 450 nm is proportional to the amount of antibody fixed, which is itself proportional to the amount of leptin present initially. The results are expressed in pg/mL of leptin present in the cell supernatants.

The samples were tested in triplicate.

4. Results

Three compositions containing 0.25, 1 and 2 μg/mL, respectively, of phytosphingosine or of its hydrochloride, were tested.

For the 3T3-F442A adipocytes which are maintained in culture without any treatment, the amount of leptin present in the culture supernatants increases strongly with time (16.4 pg/mL at D4, 802 pg/mL at D11 and 2,623 pg/mL at D20). This result is in conformity with the biological data (Leroy P. 1996, Considine R V. 1996): under basal conditions, the murine adipocytes secrete increasing amounts of leptin all throughout their maturation. We thus confirm that a mature adipocyte secretes amounts of leptin which are greater than those of a preadipocyte.

The amounts of leptin present in the supernatants are reported in Table 1 below. The abbreviation PS designates phytosphingosine.

TABLE 1

Amount of leptin, expressed in pg/mL, which is present in the culture supernatants of mature 3T3-F442A adipocytes treated with phytosphingosine at day D21

| phytosphingosine (μg/mL) | leptin (pg/mL) | |
|---|---|---|
| | Average | Standard deviation |
| 0 (control) | 1510 | 23.43 |
| 0.25 | 1789 | 11.27 |
| 1 | 1563.6 | 14.33 |
| 2 | 1428.8 | 200 |

After 7 days of treatment, i.e. at day D21, phytosphingosine induces an increase in the secretion of leptin by treated adipocytes, an effect which is maximum at the concentration of 0.25 μg/mL. The increase is of a little more than 18% at this concentration.

Phytosphingosine hydrochloride, when tested under the same conditions, is also responsible for a stimulation of the leptin secretion: +52% at 1 μg/mL and +26% at 2 μg/mL and +18% at 0.25 μg/mL. The results for the hydrochloride are reported in Table 2 below.

TABLE 2

Amount of leptin, expressed in pg/mL, which is present in the culture supernatants of mature 3T3-F442A adipocytes treated with phytosphingosine hydrochloride at day D21

| phytosphingosine-HCl (μg/mL) | leptin (pg/mL) | |
|---|---|---|
| | Average | Standard deviation |
| 0 (control) | 1510 | 23.43 |
| 0.25 | 1789 | 201.79 |
| 1 | 2301.3 | 49.821 |
| 2 | 1907.9 | 31.93 |

Thus, phytosphingosine is capable of inducing an increase in the basal adipocyte secretion of leptin in the 3T3-F442A adipose cell, a model which is very close to the human adipocyte. Phytosphingosine is thus capable of playing an important role in the control of the stability of the fatty mass.

Example 2

Demonstration of the interest in the combination of phytosphingosine with an adenylate cyclase activator, such as an extract of *Coleus forskohlii*, for promoting the decrease of lipogenesis in murine adipocytes in culture.

1. Principle of the Study

This study relates to the effects of the combination of the two actives, *Coleus forskohlii* (also named *Plectranthus barbatus*) (PB) and phytosphingosine (PS) on the recruiting of new adipocytes.

It is known that the development of white adipose tissue represents a process which is continuous throughout the whole life (AILHAUD G., GRIMALDI P., NEGREL R., Trends in Endocrinology and Metabolism, (1994) 5 (3) 132-6). The adipocyte is associated, within the adipose tissue, with an abundant extracellular matrix which also includes endothelial cells, capillaries, nerve fibres and fibroadipoblast precursors. The mature adipocyte represents the phenotype of a cell originating from the differentiation of an adipocyte precursor. The preadipocytes are present within the same adipose tissue and can be recruited at any stage of life in order to generate new adipocytes: in the case of a weight gain, an initial phase exists of increase in the adipocyte volume until a critical point is attained, which then leads to the recruitment of new cells (Bjorntorp P., Int. J. Obesity, (1991) 15 67-81). The intrinsic capacity of the preadipocytes to multiply and to differentiate into adipocytes plays a determinant role in the development of fatty masses. A hyperplasia of these cells related to the fibroblasts leads to an increase of the adipose tissue.

Thus, the mature adipocytes are firstly treated with PB+PS

Secondly, the culture medium which is conditioned with these adipocytes is placed in contact with preadipocytes the maturation of which into adipocytes will be followed.

The control cells at the start of the treatment commence to differentiate and undergo a certain number of changes: increase in volume, increase in number and of the size of the lipid droplets, increase in the activity of lipogenetic enzymes, etc.

A key enzyme in the process of synthesis of triglycerides is glycerol-3-phosphate dehydrogenase ($G_3PDH$): its specific activity increases considerably during maturation and can thus be used as a precise and sensitive measurement of adipocyte conversion (Pairault J., Green H., Proc. Nat. Acad. Sci. USA, (1979) 76, 5138-42; Koekemoer T. C. et al, Int. J. Biochem. Cell Biol. (1995) 27, 625-32).

It was chosen to follow the evolution of the activity of this enzyme in order to measure the state of differentiation of the adipocytes.

Since $G_3PDH$ is a hydrosoluble enzyme, its activity is measured in the supernatant of the cell grindings, in the presence of appropriate substrates (NADH, TEA (triethanolamine)—EDTA, 50 mM, 1 mM).

The specific activity is calculated from these determinations. The treated cells are compared with the control cells. Since $G_3PDH$ is a reflection of the state of differentiation of the cells, the higher its specific activity, the more the cells are differentiated, and vice versa: the more limited the fat reserve will be by the agent tested, more the activity of the $G_3PDH$ will be lower.

The average over three measurements with respect to a standard deviation gives an average specific activity. Then, the percentage inhibition is calculated of the inhibition of the activity of the $G_3PDH$ produced by the substances compared to the controls.

The criteria which enable ensuring the quality of good anti-lipogenetic agents are on the one hand a percentage inhibition of the enzyme which is greater than 50%, and on the other hand crude data which are significantly different with respect to the controls.

2. Material and Methods a) Culture and Treatments

The adipocytes undergoing differentiation, not very mature adipocytes, also named preadipocytes, obtained at D7 of the protocol given in Example 1 are treated with the medium which is conditioned with mature differentiated adipocytes which are not treated or treated with PB or PS and with the combination PB+PS for 8 days with a change of medium at days D9 and D11, as is indicated in the protocol below.

The phytosphingosine was tested at the final concentrations of 0.25, 0.50 and 1 µg/mL.

The extract de *Plectranthus barbatus* (PB) (batch No. 0B2, INDENA) is titrated at 80% of forskolin, a molecule which is recognised for being an effector of adenylate cyclase (Seamon K. et al., P.N.A.S. USA, (1981) 78 3363-67). The PB concentration used in the study is 25 µg/mL from a mother solution at 20 mg/mL in ethanol.

b) Preparation of the Cell Extracts

The cell plug is washed twice with PBS buffer and the cells are recovered by scratching in a 25 mM TRIS-HCl buffer, pH 7.5, containing 1 mM of EDTA at 4° C. The cells are homogenised by grinding and centrifugation at 10,000 g for 10 minutes at 4° C.

The protocol followed is summarised in the Table below.

| | |
|---|---|
| D0 | Sowing of the 3T3F442A - cell density 2 × 10⁴ cells/35 mm Petri dish. |
| | Culture medium DMEM, 5% FCS/5% CS. |
| D2 | Change of medium |
| D4 | Change of medium |
| D7 | Confluence - culture medium DMEM, 10% FCS, 1% insulin (SM 500 µg/mL) |
| | Treatment with conditioned media: PB: 0.25 µg/mL PS: 0.5 and 1 µg/mL |
| D9-D11 | Change of medium, same medium + treatment |
| D14 | Treatment, same culture medium |
| D16 | Collection of the supernatants and G₃PDH determination | c) Determination of the Glycero-3-Phosphate Dehydrogenase ($G_3PDH$) Activity.

The determination of the $G_3PDH$ activity is made according to the method of Kozak and Jensen: Kozak and Jensen, 1974, J. Biol. Chem., 249, 7775-7781.

$G_3PDH$ catalyses the following reaction:

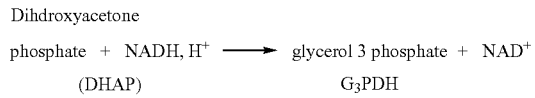

The consumption of NADH as a function of time is measured by spectrophotometry (KONTRON) at 340 nm. An absorbance variation/minute (Δ Abs/minute) can thus be calculated which corresponds to the initial rate of the enzymatic reaction. The results are expressed in specific activity (SA), i.e. in nmoles of NADH transformed/min/mg of proteins. The total protein content is evaluated by the BCA method (Protein Assay Reagent-PIERCE LTD)

$$SA = 81.25 \times \Delta Abs/min \times \frac{1}{mg \text{ of proteins}}$$

3. Results

Measurement of the glycero-3-phosphate dehydrogenase ($G_3PDH$) activity.

The amounts of NAD+ after 8 days as a function of the treatments of the cultures are reported in Table 3 below.

TABLE 3

Appreciation of the lipogenesis by measurement of the OD, expressed in nmoles NAD+, for the PB extract and for the phytosphingosine PS

| PB | PS | O.D. (nmoles NAD+) | |
|---|---|---|---|
| (µg/mL) | (µg/mL) | average | Standard deviation |
| 0 (control) | 0 (control) | 0.0016 | 0.000195 |
| 25 | 0 | 0.0004 | 0.000015 |
| 0 | 0.5 | 0.0014 | 0.00009 |
| 0 | 1 | 0.00165 | 0.00006 |
| 25 | 1 | 0.00036 | 0.00002 |
| 25 | 0.5 | 0.00043 | 0.000048 |

The results of Table 3 above are also represented in FIG. 1.

After 8 days' contact with the media which are conditioned with mature adipocytes, a slowing down of the maturation of the preadipocytes with the media containing PB (inhibition of the $G_3PDH$ activity) is observed, and this corresponds to an inhibition of the recruitment of the preadipocytes, the activity of which of the maturation marker enzyme is inhibited by 75%.

Phytosphingosine does not modify this anti-lipogenetic profile: the PS+PB combination causes between 74 and 79% of inhibition of the $G_3PDH$ activity, the 1 µg/mL PS+25 µg/mL PB combination even leads to a slowing down of the lipogenesis of these preadipocytes during maturation which is slightly greater than with PB alone.

b) Analysis of the Morphology of the Adipocytes

In parallel, the morphology of the adipocytes was analysed by direct observation of the cells in the Petri dishes, under reverse phase microscope (Olympus BH2). The cells are considered to be differentiated by morphological analysis when they acquire a round surround and that their cytoplasm is filled with lipid droplets. Inversely, a decrease in the amount of lipid vacuoles which is associated with a more elongated form gives evidence of a slowing down of this maturation.

In the presence of the PS+PB combination, the cells are characterised by a very marked delipidation of the adipocytes, which is in agreement with the lowering of the activity of the G₃PDH enzyme measured before.

FIGS. 2, 3 and 4 show, respectively:

FIG. 2: the cells of a control culture at D7. In this culture, the cells are not very differentiated, there are not many lipid vacuoles. This is the start of the treatment.

FIG. 3: the cells of a control culture at D21. The cells are loaded with lipid vacuoles.

FIG. 4: the cells of a culture treated with the 25 µg/mL PB+1 µg/mL PS combination.

c) Conclusion

This study shows that the treatment with the PB+PS combination of mature adipocytes gives information which is capable of all in all slowing down the accumulation of triglycerides in preadipocytes. The lowering of the activity of the lipogenetic enzyme G₃PDH leads to a depletion in significant intracellular lipid droplets.

The addition of phytosphingosine capable of stimulating the secretion of leptin did not inhibit the massive action of the PB on the decrease in lipids.

The maintenance of leptin in the environment close to the adipocytes could thus exert its role of signal molecule acting against the increase in the adipose mass. One is tempted to believe that a collection of cells containing cells which are emptied of a part of their content of triglycerides by lipolysis in continuing to emit a retrocontrol leptin message should contribute to the reduction of the storage of fat by the panniculus adiposus.

Example 3

Demonstration on human adipocytes in culture of the activity of phytosphingosine and of the combination of phytosphingosine with an extract of *Coleus forskohlii*, on the production of leptin and on lipolysis.

Human adipocytes originating from a plasty of a 41 year old woman, which are marketed by ZEN-BIO (USA), were used at an advanced stage of the adipocyte maturation. The reception of these cells in culture took place 16 days after sowing. They are cultivated in a specific medium ensuring their differentiation throughout the whole treatment.

D-16: sowing

D0: start of the treatment with the extract of *Coleus* (PB) and/or phytosphingosine (PS)

D6 to D18: determination of the various parameters.

The properties of *Coleus* described above for the 3T3F442A murine adipocytes were first of all verified on these human cells: lipolytic activity by measurement of the release of glycerol and non-esterified fatty acids.

Table 4 below indicates the values of glycerol release in the control cultures and cultures treated with PS.

TABLE 4

Release of glycerol, expressed in µg/mL, by human adipocytes in culture, which are non-treated or treated with 25 µg/mL of phytosphingosine, as a function of the duration of the culture

| | glycerol (pg/mL) | |
|---|---|---|
| Days | Control (PS = 0 µg/mL) | PS = 25 µg/mL |
| 3 | 73.78 | 174.4 |
| 6 | 120.8 | 196.2 |
| 9 | 147.2 | 302.9 |
| 12 | 198.4 | 416.4 |
| 15 | 196.3 | 460.6 |
| 18 | 230.9 | 659.8 |
| 21 | 276.6 | 777.1 |
| 23 | 238.9 | 687 |

It appears very clearly that the *Coleus* very strongly stimulates the adipocyte lipolysis (+128% increase in release of glycerol at 18 days with respect to the control).

It is further observed, by a measurement of release of non-esterified fatty acids, that the *Coleus* causes a strong hydrolysis of the adipocyte triglycerides in releasing, in parallel to the glycerol, a large amount of non-esterified fatty acids, at a dose of 25 µg/mL.

Other tests show that the phytosphingosine induces an increase of leptin secretion in human adipocytes as in murine adipocytes, the most effective doses being lower for the human adipocyte.

In parallel to the leptin release, phytosphingosine, at the dose of 6 ng/mL is responsible for a release of glycerol with time, without concomitant release of non-esterified fatty acids. This observation could correspond to a new form of lipolysis which is proper to leptin, and which is already described in publications.

FIGS. 5 and 6 present the evolution of the morphology of the cells under the conditions which have just been set forth.

FIG. 5 presents a control culture of human adipocytes at day D18.

A significant amount of fat vacuoles is clearly seen.

FIG. 6 presents a culture of human adipocytes at day D18, after treatment by the combination of *Coleus* (25 µg/mL) with phytosphingosine (6 ng/mL). It appears clearly that the phytosphingosine-*Coleus* combination leads to a massive and visible decrease, with lipid droplets which are less numerous and of smaller size. In parallel, a higher number of cells take up an appearance of not very mature cells (elongated form and absence of lipid vacuoles).

Thus, the combination of these two actives leads to a powerful reduction in the fat store, the modulation of leptin in the environment close to the human adipocyte being a key step in this action.

Example 4

| Slimming hydro/alcoholic formulation. | |
|---|---|
| Water | qsp 100% |
| Denatured alcohol | 42% |
| PPG-3 myristyl ether | 10% |
| Perfume | 0.20% |
| Phytosphingosine | 0.10% |

Example 5

| Slimming fluid emulsion. | |
| --- | --- |
| PPG-2 isoceteth-20 acetate | 2% |
| Poloxamer 407 | 0.50% |
| Propylene glycol isoceteth-3 acetate | 15% |
| Pentacyclomethicone | 15% |
| Water | qsp.100% |
| Butylene glycol | 3% |
| Preservatives | q.s. |
| Extract of *Coleus forskohlii* (at 80% of forskolin) | 0.1% |
| Xanthan gum | 0.05% |
| Acrylates/c10-30 alkyl acrylate cross-polymer | 0.04% |
| Neutraliser | q.s. |
| Polyacrylamide c13-14 isoparaffin laureth-7 | 0.50% |
| Perfume | 0.20% |
| Phytosphingosine | 0.05% |

Example 6

| Slimming cream. | |
| --- | --- |
| Steareth-2 | 0.50% |
| Steareth-21 | 1.75% |
| Cetyl alcohol | 0.30% |
| Stearyl alcohol | 0.30% |
| Stearic acid | 0.50% |
| 2-ethylhexyl stearate | 4.00% |
| Cetearyl isononanoate | 3.00% |
| Squalane | 4.00% |
| IBMX | 1.00% |
| Dimethicone | 0.40% |
| Water | qsp.100.00% |
| Glycerine | 2.00% |
| Butylene glycol | 3.00% |
| Preservatives | q.s. |
| Acrylates/c10-30 alkyl acrylate cross-polymer | 0.35% |
| Xanthan gum | 0.10% |
| Sodium hyaluronate | 0.02% |
| Neutraliser | q.s. |
| Polyacrylamide c13-14 isoparaffin laureth 7 | 0.50% |
| Denatured alcohol | 5.00% |
| Perfume | 0.20% |
| Phytosphingosine | 0.002% |

The invention claimed is:

1. A method of cosmetic care for obtaining a slimming effect on the human body, comprising the application on the parts of the body in need thereof of at least one slimming active agent comprising at least phytosphingosine or phytosphingosine cosmetically acceptable salts, present in a cosmetic composition in a concentration of between 0.001% and 1%, by weight with respect to the total weight of said composition.

2. The method according to claim 1, wherein said method is intended for reducing subcutaneous excess fat.

3. The method according to claim 1, wherein said phytosphingosine cosmetically acceptable salt is phytosphingosine hydrochloride.

4. The method according to claim 1, wherein said method further comprises applying at least one cosmetically acceptable lipolytic agent.

5. The method according to claim 4, wherein said lipolytic agent is selected from the group consisting of adenosine-3', 5'-cyclic monophosphate (cAMP) and its cosmetically acceptable derivatives.

6. The method according to claim 5, wherein said cosmetically acceptable derivatives are selected from the group consisting of the salts and acylated derivatives of cAMP.

7. The method according to claim 6, wherein said derivative is selected from the group consisting of mono- and dibutyril derivatives of cAMP.

8. The method according to claim 5, wherein said cAMP or said lipolytic agent is at a concentration of between 0.001% and 5%, by weight with respect to the total weight of said composition.

9. The method according to claim 4, wherein said lipolytic agent is an adenylate cyclase enzyme activating agent.

10. The method according to claim 9, wherein said adenylate cyclase enzyme activating agent is selected from the group consisting of forskolin and plant extracts containing the same.

11. The method according to claim 10, wherein said adenylate cyclase enzyme activating agent is at a concentration of between 0.001% and 1%, by weight with respect to the total weight of said composition.

12. The method according to claim 10, wherein said adenylate cyclase enzyme activating agent is selected from the group consisting of extracts of *Coleus forskohlii* and *Plectranthus barbatus*.

13. The method according to claim 10, wherein said adenylate cyclase activating agent is an extract of the plant *Tephrosia purpurea*, at a concentration of between 0.001% and 5% by weight, with respect to the total weight of said composition.

14. The method according to claim 4, wherein said lipolytic agent is a phosphodiesterase enzyme inhibiting agent.

15. The method according to claim 14, wherein said phosphodiesterase enzyme inhibiting agent is selected from the group consisting of xanthines, IBMX, caffeine and theophylline.

16. The method according to claim 15, wherein said phosphodiesterase enzyme inhibiting agent is 3-isobutyl-1-methyl-xanthine.

17. The method according to claim 15, wherein said phosphodiesterase enzyme inhibiting agent is at a concentration of between 0.001% and 10% by weight, with respect to the weight of said composition.

\* \* \* \* \*